(12) United States Patent
Isogai et al.

(10) Patent No.: US 7,737,323 B2
(45) Date of Patent: Jun. 15, 2010

(54) ABSORBENT ARTICLE

(75) Inventors: Kazunari Isogai, Kagawa-ken (JP); Tomoko Sugito, Kagawa-ken (JP)

(73) Assignee: Uni-Charm Corporation, Ehime-ken (JP)

( * ) Notice: Subject to any disclaimer, the term of this patent is extended or adjusted under 35 U.S.C. 154(b) by 623 days.

(21) Appl. No.: 11/533,966

(22) Filed: Sep. 21, 2006

(65) Prior Publication Data
US 2007/0100305 A1 May 3, 2007

(30) Foreign Application Priority Data
Oct. 31, 2005 (JP) .............................. 2005-317363

(51) Int. Cl.
*A61F 13/15* (2006.01)
*A61F 13/20* (2006.01)

(52) U.S. Cl. ....................................... 604/361; 604/383

(58) Field of Classification Search .................. 604/361
See application file for complete search history.

(56) References Cited

U.S. PATENT DOCUMENTS

2005/0222547 A1* 10/2005 Beruda et al. ............... 604/368

FOREIGN PATENT DOCUMENTS

| JP | 09140742 | 6/1997 |
|---|---|---|
| JP | 09299401 | 11/1997 |
| JP | 10075980 | 3/1998 |
| JP | 11169403 | 6/1999 |
| JP | 2002153503 | 5/2002 |
| JP | 2002153504 | 5/2002 |
| JP | 2002153505 | 5/2002 |
| JP | 2002209934 | 7/2002 |
| JP | 2003070837 | 3/2003 |
| JP | 2003516185 | 5/2003 |
| JP | 2004208833 | 7/2004 |
| JP | 2004-337386 A | 12/2004 |
| JP | 2005-027884 A | 2/2005 |
| JP | 2005152264 | 6/2005 |
| WO | 0141691 | 6/2001 |

OTHER PUBLICATIONS

English translation of JP 2005-027884 to Sugiyama.*
English translation of JP 2004-337386 to Ichimada.*
International Search Report of PCT/JP2006/318263 issued Oct. 10, 2006.

* cited by examiner

*Primary Examiner*—Melanie J Hand
(74) *Attorney, Agent, or Firm*—Lowe Hauptman Ham & Berner LLP (57) ABSTRACT

An absorbent article is provided which has such a structure that a bled portion of the colored indicator is unnoticeable. The absorbent article includes a liquid permeable top sheet, a liquid impermeable back sheet, an absorbing core interposed between the two sheets, and an indicator making it possible to visually ascertain that the absorbing core is in the wet state. The back sheet has an average hole diameter of 0.3 μm to 3 μm, and has a light transmittance of not less than 20% and not more than 45% in a state in which the absorbing core is dry.

13 Claims, 6 Drawing Sheets

ABSORBENT ARTICLE

This application is based on and claims the benefit of priority from Japanese Patent Application No. 2005-317363, filed on 31 Oct. 2005, the content of which is incorporated herein by reference.

BACKGROUND OF THE INVENTION

1. Field of the Invention

The present invention relates to an absorbent article that absorbs body fluids, such as a disposable diaper, and particularly to an absorbent article with an indicator making it possible to visually ascertain whether an absorbent core in an absorbent article is wet.

2. Related Art

Conventionally, it has been known to provide an indicator in an absorbent article, such as a disposable diaper and a urine-absorbing pad, so that the excretion of urine can be ascertained from the outside of a liquid impermeable back sheet, namely from the outside when the absorbent article is worn. This indicator is positioned between the back sheet and an absorbent core of the absorbent article, and contains an indicating agent whose color shows clearly when wetting occurs.

For example, Japanese Unexamined Patent Publication No. H9-299401 discloses that an indicator includes an ink layer which shows clearly when wetting occurs and an ink covering layers which are interposed between the ink layer and a back sheet and are close contact with the ink layer, and that the ink covering layer contains a surface active agent.

On the other hand, Japanese Unexamined Patent Publication No. 2003-516185 discloses an absorbent article provided with an indicator that consists of an indicating agent whose color shows clearly when wetting occurs, and a base polymer. This absorbent article prevents the indicator from generating an error signal due to moisture, by employing a moisture permeable film as a back sheet.

In the indicator disclosed in the above publication No. 9-299401, a moisture absorbing paper is used as the ink covering layer, and the ink layer is formed by printing ink on this paper. The application of the indicator including this ink layer to a diaper may ruin its soft touch. Further, for the paper used in this ink layer, the absorbed urine is susceptible to diffusion into the paper. Therefore, when viewed from the outside of the back sheet, in some cases, the colored indicator may be blurred. If this is the case, it is difficult to distinguish the wet region of the absorbent core by using the indicator. Further in some cases, the ink of the indicator may diffuse into its surroundings and the colored portion may fade away. For this reason, it might be difficult for the indicator disclosed in the above publication No. 9-299401 to accurately indicate when to replace the diaper.

Similarly, for the absorbent article disclosed in the above publication No. 2003-516185, no attention has been paid to the preventing from bleeding of the color indicator, to make it unnoticeable.

In view of the foregoing, it is an object of the present invention to provide an absorbent article having a structure such that a bled portion of a colored indicator is unnoticeable, thus making it possible to accurately indicate the timing for replacement.

SUMMARY OF THE INVENTION

The present inventors have achieved the present invention based on the finding that a bled portion of a colored indicator can be made unnoticeable by adjusting the light transmittance and the average hole diameter of a back sheet.

A first aspect of the present invention is an absorbent article including: a liquid permeable top sheet; a liquid impermeable back sheet; an absorbing core interposed between the top sheet and the back sheet; a covering material that covers the absorbing core; and an indicator being interposed between the back sheet and the covering material, the indicator making it possible to visually ascertain that the absorbing core and the covering material are wet. The back sheet has an average hole diameter of 0.3 µm to 3 µm, and has a light transmittance of not less than 20% and not more than 45% in a state in which the covering material is dry.

According to the first aspect of the present invention, the absorbent article in which the bleeding of the colored indicator can be unnoticed can be provided by adjusting the average hole diameter of the back sheet to 0.3 µm to 3 µm, and the light transmittance of the back sheet to not less than 20% and not more than 45% in a state in which the covering material is dry. This enables a person replacing the article (for example, a caretaker or a mother) to be accurately informed of the timing of replacement of the absorbent article.

Further, the covering of the absorbing core with the covering material suppresses the bleeding of the colored indicator. This makes the bled portion less noticeable when the colored indicator is viewed through the back sheet. The covering material is required to cover at least the surfaces parallel to the longitudinal direction of the absorbing core. Preferably, it covers the entire surface of the absorbing core.

As used herein, the term "absorbent article" means an article that absorbs body fluids. Specifically, it means an infant diaper, a nursing care diaper, and a urine-absorbing pad. The term "wet state" means the state in which the absorbing core contains 5% or more moisture relative to its own weight. The term "covering material" means a sheet having a thickness of 0.07 mm to 3.0 mm. There are, for example, tissue paper, and a spun bond/melt blown/spun bond nonwoven fabric (hereinafter referred to as an SMS nonwoven fabric), and the like.

The expression "a state in which the covering material is dry" means the state in which both of the absorbing core and the covering material are dry, and the state in which only the covering material is dry. That is, it does not mean the absolutely dry state, and includes the case of containing moisture to the extent that the indicator produces no color.

A second aspect of the absorbent article as described in the first aspect of the present invention provides an absorbent article wherein the back sheet has water-vapor permeability.

According to the second aspect of the present invention, imparting water-vapor permeability to the back sheet provides the absorbent article that enables a wearer to comfortably wear it without feeling uncomfortable under humid and hot conditions.

A third aspect of the absorbent article described in the first or the second aspect of the present invention provides an absorbent article in which the indicator is applied to the back sheet in a weight of 10 g/m² to 35 g/m².

According to the third aspect of the present invention, applying the indicator in a weight of 10 g/m² to 35 g/m² makes it easy to observe from above the back sheet a discoloration difference before and after the indicator produces a color. This enables a person replacing the article to accurately know the timing of replacement of the absorbent article. Preferably, the indicator is applied by the hot melt method, for ease of manufacturing.

A fourth aspect of the absorbent article described in the first through third aspect of the present invention provides an absorbent article in which the covering material is a nonwoven fabric that is treated so as to have a hydrophilic property.

According to the fourth aspect of the present invention, by employing the nonwoven fabric that is treated so as to have a hydrophilic property as the covering material, it is possible to make the bled portion even less noticeable when the colored indicator is viewed through the back sheet. As used herein, the term "nonwoven fabric that is treated so as to have a hydrophilic property" means an SMS nonwoven fabric, a spun bond/melt blown nonwoven fabric (an SM nonwoven fabric), or a spun bond nonwoven fabric (an SB nonwoven fabric).

Thus, the present invention is capable of providing an absorbent article in which the bleeding of the colored indicator appears to be reduced by adjusting each of the average hole diameter and the light transmittance of the back sheet to a predetermined value. This enables the person replacing the article (for example, the caretaker or the mother) to be accurately informed of the timing of replacement of the absorbent article.

DETAILED DESCRIPTION OF THE INVENTION

Preferred embodiments of the present invention will be described below.

First Embodiment

Figure 1:
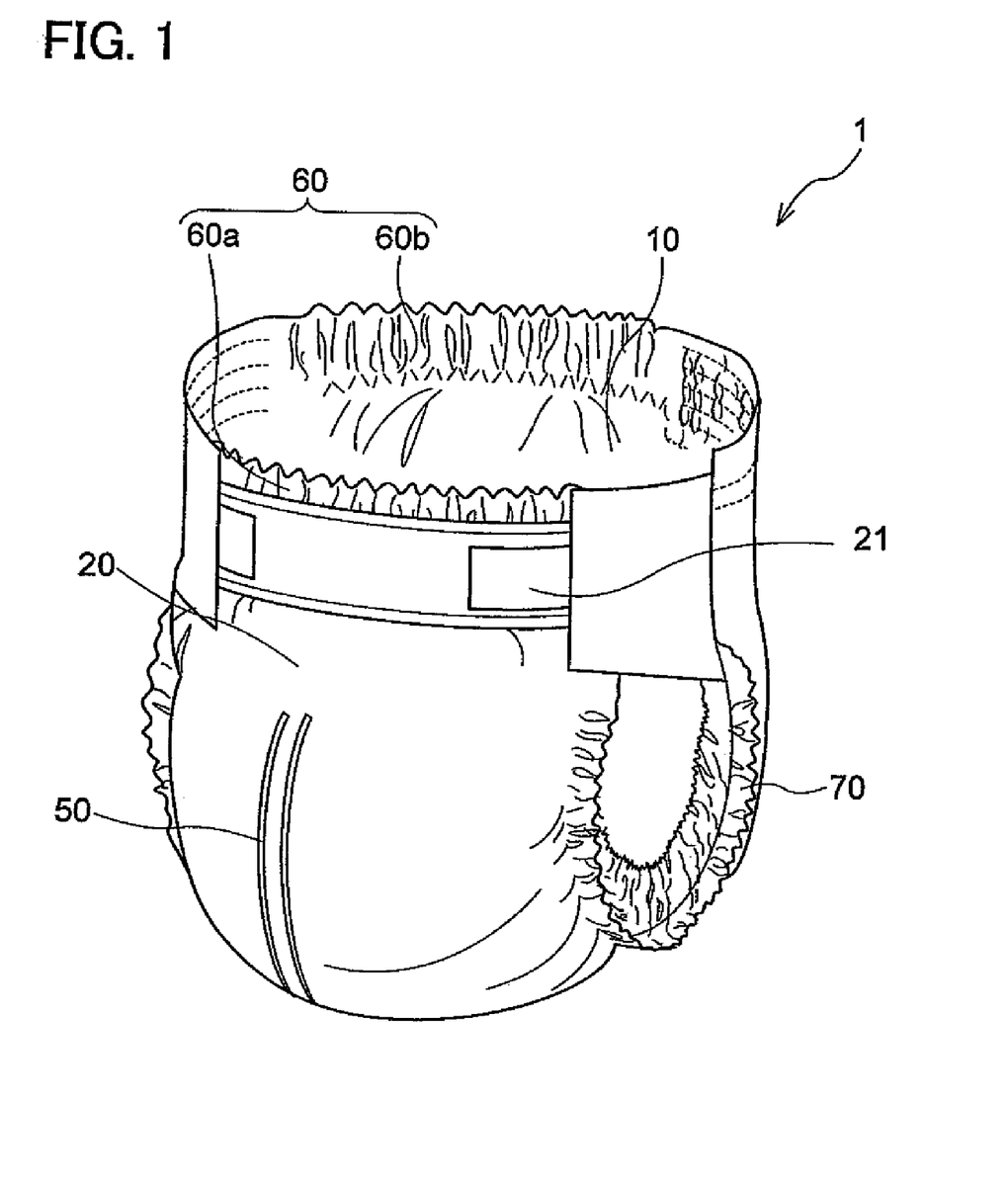
FIG. 1 is a diagram showing an absorbent article according to the first embodiment of the present invention.
Figure 2:
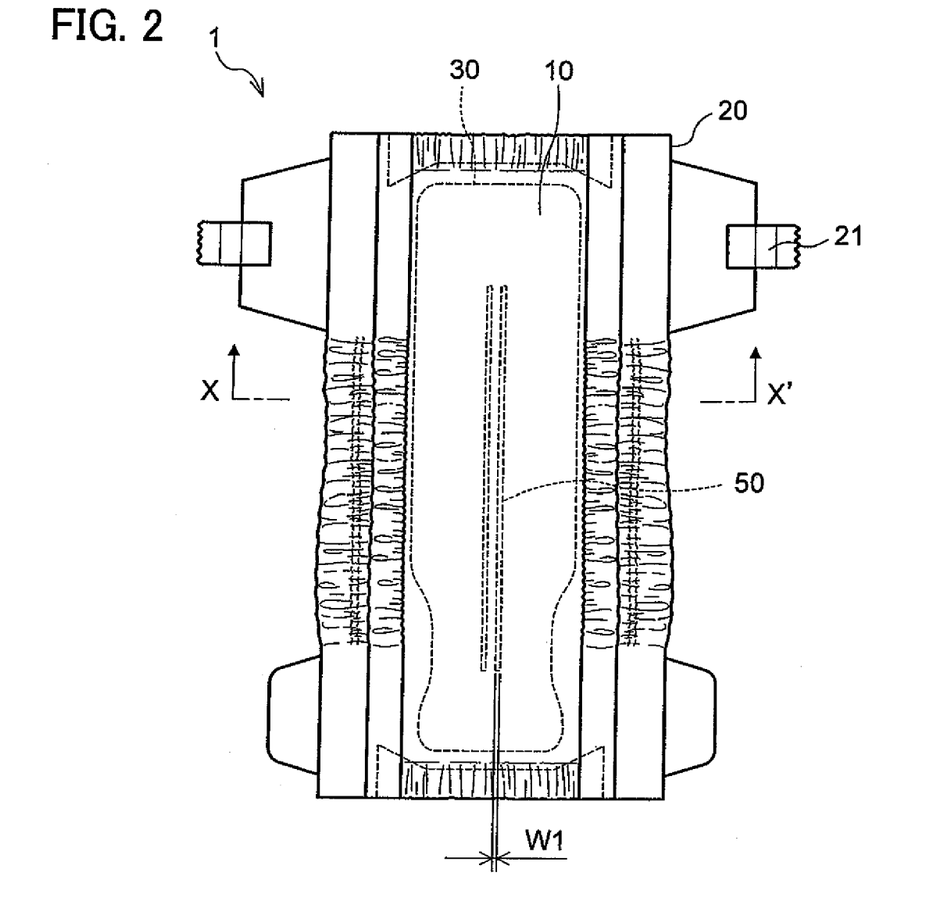
FIG. 2 is an exploded view of the absorbent article of the first embodiment.

FIG. 1 shows a case where an absorbent article 1 of the present invention is manufactured as a diaper. FIG. 2 is an exploded view of the absorbent article 1. The absorbent article 1 has a top sheet 10 that is in contact with the skin of a wearer during wear, a back sheet 20 that functions as an outer of the absorbent article 1, an absorbing core 30 that is wrapped by the sheets 10 and 20, and a covering material 31 that encases the absorbing core 30. Further, an indicator 50 is disposed between the covering material 31 and the back sheet 20. The absorbing core 30, the covering material 31, and the indicator 50 are arranged so as to cover the crotch and its surroundings.

The absorbent article 1 is further provided with a front girth region 60a, a rear girth region 60b, and a crotch region interposed between these girth regions 60. The side edge portions of the girth region 60 are stacked one upon another with the top sheet 10 facing to the inside. The rear girth region 60b of the back sheet 20 has a pair of fastening tapes 21, enabling fastening during wear. The absorbent article 1 further includes a pair of leg openings 70. The leg openings 70 and the girth region 60 are completely or partially provided with a stretching member (not shown) so as to improve adhesion during the wear.

Figure 3:
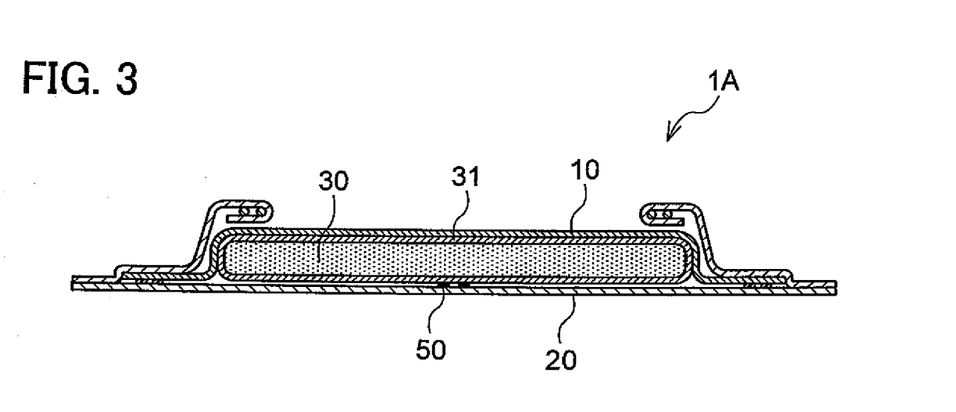
FIG. 3 is a sectional view of the absorbent article of the first embodiment.

FIG. 3 shows schematically a cross section taken along the line X-X' in the absorbent article 1 of FIG. 2. The indicator 50 is disposed between the back sheet 20 and the covering material 31. The indicator 50 contains a hot melt adhesive so that it can be connected to the back sheet 20 by hot melting. Preferably, the indicator 50 is applied to the back sheet 20 in a weight of 10 $g/m^2$ to 35 $g/m^2$, and more preferably 15 $g/m^2$ to 30 $g/m^2$. When the weight is below 10 $g/m^2$, the color change before and after the indicator produces a color is unclear, resulting in degradation of the function as the indicator. When the weight is over 35 $g/m^2$, the bleeding component is increased, and the bleeding shows clearly from the outside of the back sheet 20.

Preferably, a width $W_1$ of the indicator 50 is 0.5 mm to 5 mm, and more preferably 1.5 mm to 2.5 mm. When the width is below 0.5 mm, the coloring of the indicator 50 is unclear. When the width is over 5 mm, the bleeding of the colored indicator 50 tends to be prominent.

Figure 4A:
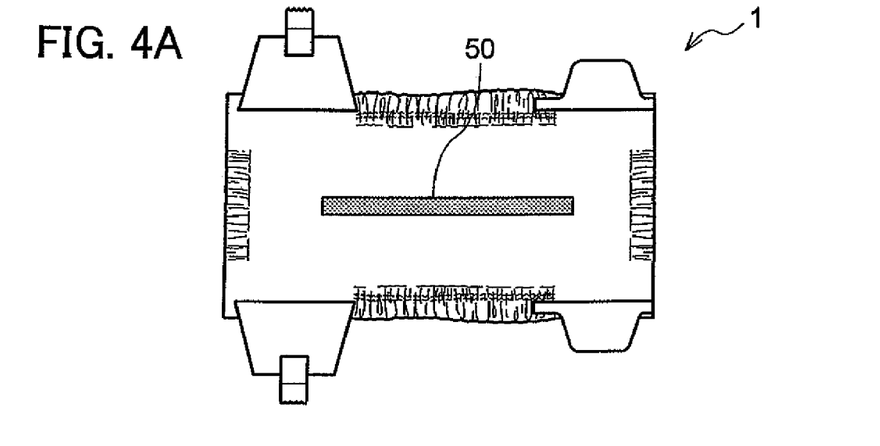
FIGS. 4A to 4C are exploded views of the absorbent article of the first embodiment.
Figure 4B:
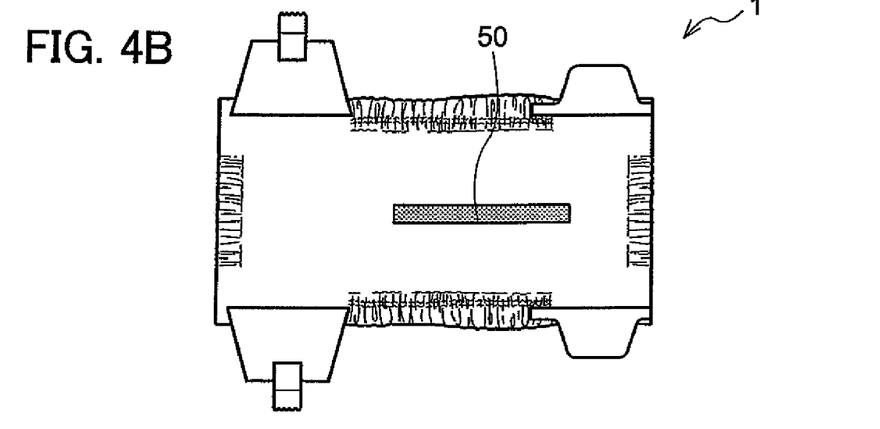
Figure 4C:
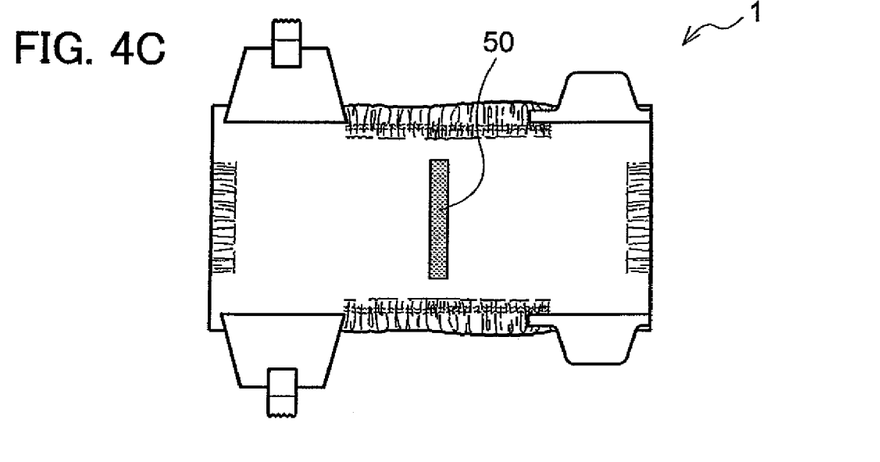

In the present embodiment, the indicator 50 is disposed at the substantially middle part in the widthwise direction of the absorbing core 30 and the covering material 31, and along the lengthwise direction. The position is not limited to this, and the indicator 50 may be disposed at any position corresponding to the crotch of the wearer and its surroundings. Specifically, as shown in FIG. 4A, the indicator 50 may be disposed at the substantially middle part in the widthwise direction of the absorbing core 30, and in parallel to the lengthwise direction. Alternatively, as shown in FIG. 4B, the indicator 50 may be disposed at the substantially middle part in the widthwise direction of the absorbing core 30 and the covering material 31, and in parallel to the lengthwise direction. Alternatively, as shown in FIG. 4C, the indicator 50 may be disposed at the substantially middle part in the lengthwise direction of the absorbing core 30 and the covering material 31, and in parallel to the widthwise direction.

The shape of the indicator 50 is not limited as far as the indicator 50 can be visually recognized through the back sheet 20. The indicator 50 of the first preferred embodiment is in the shape of two lines.

The respective components of the absorbent article 1 will be described below.

Back Sheet

A plastic film or a nonwoven fabric laminated on the external surface of a plastic film is used as the back sheet 20. The first embodiment employs the plastic film. Preferably, the light transmittance of the back sheet 20 is not less than 20% and not more than 45% in a state in which the absorbing core 30 is dry, and more preferably not less than 30% and not more than 40%. When the light transmittance is below 20%, even when the indicator 50 produces a color, it might be invisible through the back sheet 20. When the light transmittance is over 45%, the bled part shows clearly from the outside of the back sheet 20.

The back sheet 20 also has fine holes in order to adjust moisture-vapor permeability. Preferably, the average hole diameter of the holes is 0.3 μm to 3 μm, and more preferably 0.5 μm to 2 μm. When the average hole diameter of the holes is below 0.3 μm, moisture does not readily escape, and humid and hot conditions may occur. When the average hole diameter of the holes is over 3 μm, in case the applied indicator 50 is allowed to stand under high temperatures for a long time (for example, at 50 degrees Celsius for 48 hours), the fluidized indicator 50 may enter and spread into the holes, so that the bleeding of the colored indicator 50 is clearly evident.

For example, the holes of the back sheet 20 can be obtained by incorporating an inorganic filler such as calcium carbonate into the sheet, followed by drawing.

The back sheet 20 has water-vapor permeability. Preferably, the moisture-vapor permeability of the back sheet 20 is 1500 g/m$^2$·24 h to 4000 g/m$^2$·24 h, and more preferably 2000 g/m$^2$·24 h to 3000 g/m$^2$·24 h. When the water-vapor permeability of the back sheet 20 is below 1500 g/m$^2$·24 h, the wearer might have skin problems such as prickly heat or rashes. When the water-vapor permeability of the back sheet 20 is over 4000 g/m$^2$·24 h, after the wearer egests, it may become difficult to suppress the odor of excrement.

Indicator

The indicator 50 contains a base polymer and an indicating agent. Preferably, the base polymer has hydrophobic property to the extent that coloring can be suppressed in a state in which the absorbing core 30 is dry. Preferably, the weight-average molecular weight of the base polymer is 2,000 to 10,000, and more preferably 5,000 to 8,000. When the weight-average molecular weight of the base polymer is below 2,000, the indicator 50 may take a solution or wax state, and as a result, the moisture in an air atmosphere will be easily dissolved in the indicator 50, and in some cases, this might generate an erroneous indication.

Examples of the base polymer are polyethylene glycol, polypropylene glycol, polyethylene glycol-polypropylene glycol block copolymer, ethoxylated branched aliphatic diol, ethoxylated aliphatic alcohol and carboxylic acid, fatty acid polyethylene glycoldiester, and polyalkylene oxide polysiloxane, and mixtures of these. There may further be used glycerine, dodecyl amine, 2,4,4-trimethyl-2-oxazoline, N,N-di(polyoxyethylene)ethyl amine, polyoxypropylene-diethyl amine complex adducts, and nonionic surface active agents such as polyoxyethylene lauryl ether, polyoxyethylene oleyl ether, polyoxyethylene nonylphenyl ether, polyoxyethylene sorbitan monolaurate, polyethylene glycol monostearate.

The base polymer is contained in the indicator 50 in a range of about 20 mass % to 99 mass %, and preferably 30 mass % to 95 mass %, and particularly preferably 40 mass % to about 90 mass %. When the base polymer content is below 20 mass %, the indicating agent may produce a color even with moisture in the air. When the base polymer content is over 99 mass %, even when the indicating agent produces a color, it may be visually unrecognizable from the back sheet.

The indicator 50 further contains the indicating agent. Examples of the indicating agent are acid base indicating agents whose color is changed in response to a change of pH, such as ethyl red, bromophenol blue, bromocresol green, and resazurin; and dyes which are essentially invisible in the dry composition thereof, and the color of which is changed with moisture. Among these, ethylene red, bromophenol blue, and bromocresol green, each of which has a pH of about 3.5, are suitable.

The indicating agent is contained in the indicator 50 in a range of about 1 mass % to 80 mass %, and preferably 5 mass % to 70 mass %, and particularly preferably 10 mass % to about 60 mass %. When the indicating agent content is below 1 mass %, in case in which a wetness indicating agent is contained, it is difficult to observe the color change of the wet indicating agent. When the indicating agent content is over 80 mass %, the indicating agent may produce a color even with moisture in the air.

The indicator 50 is made into an adhesive by hot melting, and hence contains at least one of thickened resin, plasticizing oil, and wax diluent. Examples of the thickened resin are natural and denatured rosins such as gum rosin, wood rosin, tall oil rosin, distilled rosin, hydrogenated rosin, dimerized rosin, and polymerized rosin. The above-mentioned thickened resin is contained in the indicator 50 in a range of 10 mass % to 40 mass %.

The sensitivity of the indicator 50 is such that, in the state of an absorbent article, the color is changed from yellow to blue within two minutes after 5 cc of physiological salt solution is dropped from the liquid permeable top sheet 10.

Covering Material

Tissue paper or an SMS nonwoven fabric can be used as the covering material 31. The first preferred embodiment employs tissue paper. Preferably, the covering material has a thickness of 0.07 mm to 3.0 mm, and more preferably 0.1 mm to 0.3 mm. When the thickness is below 0.07 mm, it is difficult to maintain the strength as the covering material. When the thickness is over 3.0 mm, the wearer might feel uncomfortable.

Top Sheet

A liquid permeable sheet such as of hydrophilic nonwoven fabric or perforated plastic can be used as the top sheet 10. As used herein, the term "nonwoven fabric" means one made by manufacturing methods such as spun bond, spun race, needle punch, melt brown, thermal bond, chemical bond, and air through fabrics. Examples of the nonwoven fabric are polyolefin, polyester, and polyamide fabrics; core/sheath complex fabrics formed of polyethylene, polypropylene, or polyester; and side-by-side fabric. The embodiment employs an air through fabric of a complex fabric of polyethylene and polypropylene. When a perforated plastic film is used, the suitable hole diameter is 0.5 mm to 3 mm.

Stretching Member

A plastic sheet formed of a natural rubber, a synthetic rubber, or a thermoplastic synthetic resin can be used as an stretching member. The first preferred embodiment employs a natural rubber.

Absorbing Core

As the absorbing core 30, one consisting of a hydrophilic fabric and a high absorptive polymer can be used. Examples of the hydrophilic fabric are absorptive fabrics such as pulp, rayon, acetate, and cotton; and fabrics that are treated so as to impart a hydrophilic property to a thermoplastic synthetic resin. The present embodiment employs pulp. In order to prevent the retained body fluid from leaking, a plastic film may be disposed on the surface opposed to the back sheet 20.

Second Embodiment

Figure 5:
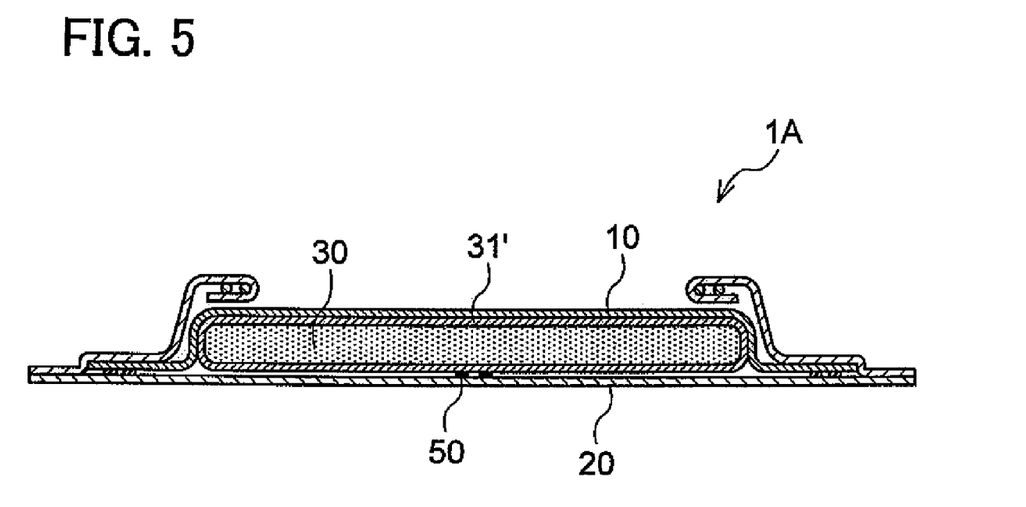
FIG. 5 is a sectional view of an absorbent article according to a second embodiment of the present invention.

A second embodiment is different from the first embodiment in that an SMS nonwoven fabric is used as the covering material. FIG. 5 is a sectional view of an absorbent article 1A according to the present embodiment. The whole of the absorbing core 30 is covered with a covering material 31' formed of the SMS nonwoven fabric. This construction has further effectiveness in preventing the bleeding of the colored indicator 50.

Preferably, the covering material 31' has a thickness of 0.07 mm to 0.7 mm, and more preferably 0.1 mm to 0.4 mm. When the thickness is below 0.07 mm, it is difficult to maintain the strength as the covering material. When the thickness is over 0.7 mm, the wearer might feel uncomfortable.

Third Embodiment

Figure 6:
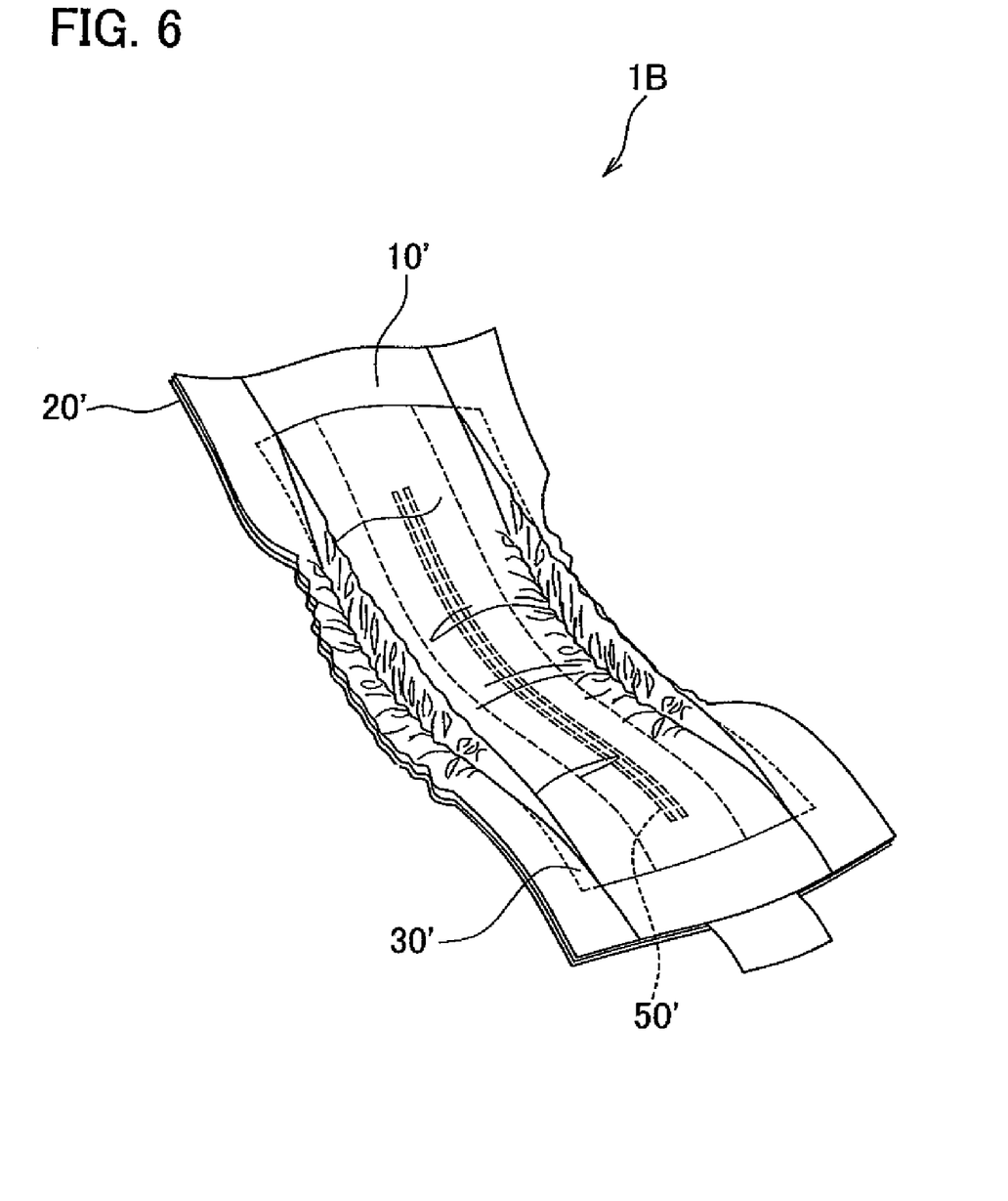
FIG. 6 is a diagram showing an absorbent article according to a third embodiment of the present invention.
Figure 7A:
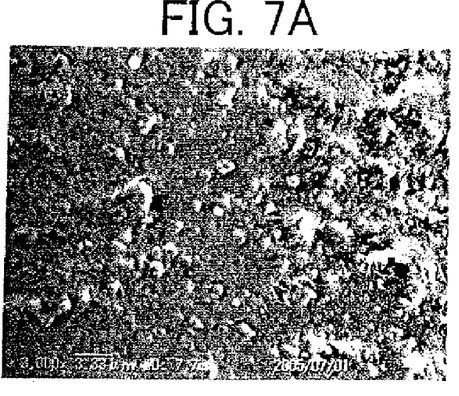
FIG. 7A is an electron micrograph of the surface of the back sheet used in the sample 1.
Figure 7B:
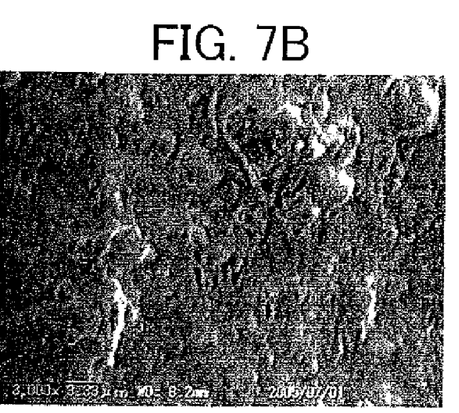
FIG. 7B is an electron micrograph of the surface of the back sheet used in the sample 2.
Figure 7C:
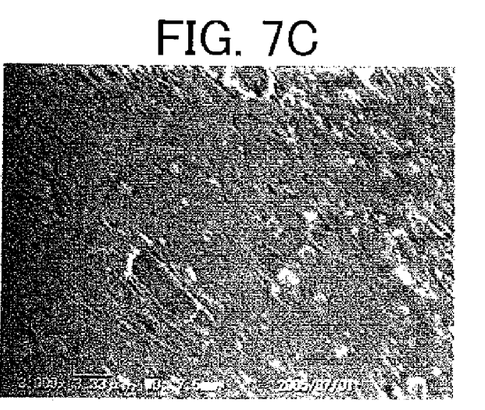
FIG. 7C is an electron micrograph of the surface of the back sheet used in the example 3.
Figure 7D:
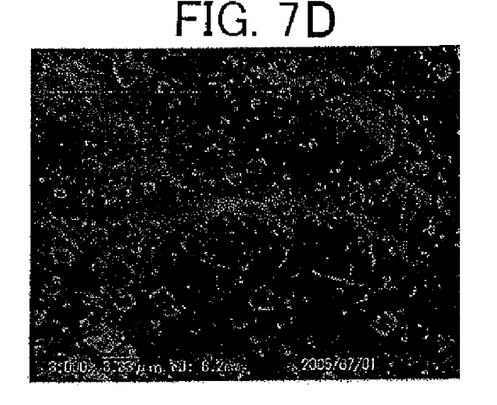
FIG. 7D is an electron micrograph of the surface of the back sheet used in the example 4.

This explains the case where the absorbent article of the present invention is applied to a urine-absorbing pad. Referring to FIG. 6, as in the foregoing embodiments, an absorbent article 1B has a liquid permeable top sheet 10, an absorber 30' that absorbs and retains liquid, and a liquid impermeable back sheet 20'. Further, a stretching member is provided at the widthwise ends (the locations corresponding to the periphery of legs) of the absorbent article 1B. Additionally, a holding means for holding the absorbent article 1B to an undergarment (namely "magic tape" (a registered trademark) in the present embodiment) is provided on the reverse surface side and the substantially middle part of the absorbent article 1B.

The urine-absorbing pad according to the present invention will be described in more detail. In the absorbent article 1B, the absorber 30' overlies the back sheet 20', and the top sheet 10' is disposed so as to wrap the absorber 30'. Further, an indicator 50' is disposed between the back sheet 20' and the absorber 30' in the same manner as in the foregoing embodiments.

Although no particular limitation is imposed on the position of the indicator 50', an area close to a urination point is more preferred.

EXAMPLES

The followings are the results of comparative tests of the bleeding in the wet state in the indicator of the absorbent article of the present invention. Models of absorbent articles were used as samples. These models were manufactured under the same conditions except for the light transmittance and the average hole diameter of the back sheet. Details of the conditions are shown in the following Table 1.

TABLE 1

|  | Sample 1 | Sample 2 | Sample 3 | Sample 4 |
|---|---|---|---|---|
| Weight (g/m$^2$) | 22 | 22 | 22 | 22 |
| Light transmittance (%) | 40.7 | 55.4 | 42.3 | 67.9 |
| Moisture-vapor permeability (g/m$^2$ · 24 h) | 3000 | 1970 | 3040 | 1841 |
| Maximum hole diameter (μm) | 1.8 | 2.5 | 7.5 | 1.7 |
| Coating weight (g/m$^2$) | 35 | 35 | 35 | 35 |
| Color bleeding | G | B | G | B |
| HMA thick bleeding | G | G | B | G |

FIGS. 7A to 7D show the electron micrographs of the back sheets used in the above samples. In these micrographs, substantially circular dark portions are holes. The light transmittance of the sheet piece of each sample having a width 50 mm×40 mm was measured on a turbidity and condensation measuring instrument (NDH-300A manufactured by Nippon Denshoku Kogyo Co., Ltd.) in accordance with JIS-K7105 of the Japanese Industrial Standards which is a testing method for optical properties of plastics, n=10 is measured, and the value is calculated by the average.

The water-vapor permeability of each of the sheets was determined according to JIS-Z-0208 which is a testing method for determination of the water-vapor transmission rate of moisture-proof packaging materials (dish method). First, 20 cc of water was poured into a circular cup (60 mm in φ), and wax was melted at 100 degrees Celsius. The mouth of the cup was then subjected to sealing wax with each sheet piece, thereby obtaining a test sample. After this sample was allowed to stand at 20 degrees Celsius and a humidity of 60% for 30 minutes, its weight was measured to obtain a numerical value (A). Thereafter, this sample was further allowed to stand at 40 degrees Celsius and a humidity of 60% for 24 hours, and its weight was measured to obtain a numerical value (B). These values (A) and (B) were substituted into the following equation calculated from the average for n=5.

Water-vapor permeability=$(B-A)/(\pi \times 0.03 \times 0.03)$

Further, the average hole diameter of each sheet was determined with an electron microscope (called "Real Surface View Electron Microscope VE-7800," manufactured by Keyence Corporation).

Bleeding tests of Sample 1 to Sample 4 were conducted. That is, a 200 cc of physiological salt solution at 40 degrees Celsius was poured from the top sheet side. After this was allowed to stand for five minutes, the bleeding of the indicator was visually ascertained from the back sheet side. The results are shown in the lower part of Table 1, wherein the mark "B" indicates the occurrence of bleeding, and the mark "G" indicates no bleeding. It will be noted from Table 1 that Sample 1 of the present invention showed neither color bleeding nor thick bleeding ("HMA thick bleeding" in Table 1), whereas the other samples (Samples 2, 3, and 4) showed one of them.

While preferred embodiments of the present invention have been described and illustrated above, it is to be understood that they are exemplary of the invention and are not to be considered to be limiting. Additions, omissions, substitutions, and other modifications can be made thereto without departing from the spirit or scope of the present invention. Accordingly, the invention is not to be considered to be limited by the foregoing description and is only limited by the scope of the appended claims.

What is claimed is:

1. An absorbent article comprising:
 a liquid permeable top sheet;
 a liquid impermeable back sheet;
 an absorbing core interposed between the top sheet and the back sheet;
 a covering material surrounding said absorbing core; and
 an indicator being directly sandwiched between the back sheet and the covering material, and including an indicating agent a color of which is changed when wet for providing a visual indication when the absorbing core and the covering material are in a wet state,
 wherein the back sheet has
 a plurality of through holes and an average hole diameter of the through holes is 3 μm to 3 μm, and
 a light transmittance in a range between 20% and 45%,
 wherein the covering material is positioned between the top sheet and the back sheet and directly attached to the top sheet, and
 wherein said indicator directly contacts the back sheet and the covering material.

2. The absorbent article according to claim 1, wherein the back sheet has water-vapor permeability.

3. The absorbent article according to claim 1, wherein the indicator is directly applied to the back sheet in a weight of 10 g/m$^2$ to 35 g/m$^2$.

4. The absorbent article according to claim 1, wherein the covering material comprises a hydrophilically treated nonwoven fabric.

5. The absorbent article according to claim 2, wherein the indicator is directly applied to the back sheet in a weight of 10 g/m$^2$ to 35 g/m$^2$.

6. The absorbent article according to claim 2, wherein the covering material comprises a hydrophilically treated nonwoven fabric.

7. The absorbent article according to claim 3, wherein the covering material comprises a hydrophilic nonwoven fabric.

8. The absorbent article according to claim 1, wherein said indicating agent is contained in the indicator in a range of 1 mass % to 80 mass %.

9. The absorbent article according to claim 1, wherein said indicator comprises at least a strip elongated in a longitudinal direction in the absorbing core and has a width in a transverse direction of the absorbent core in a range of 0.5 mm to 5 mm.

10. The absorbent article according to claim 9, wherein said indicator consists of one said strip.

11. The absorbent article according to claim 9, wherein said strip is displaced toward a front waist region of the article without extending to a rear waist region of the absorbent article.

12. The absorbent article according to claim 1, wherein said indicator comprises at least a strip elongated in a transverse direction in the absorbing core.

13. The absorbent article according to claim 8, wherein said indicator further comprises a base polymer which is contained in the indicator in a range of 20 mass % to 99 mass %.

* * * * *